(12) United States Patent
Williams

(10) Patent No.: US 11,406,511 B2
(45) Date of Patent: Aug. 9, 2022

(54) LATERAL SPINE PLATE WITH LATERAL SPINE CAGE ANCHORING SYSTEM

(71) Applicant: Seth K. Williams, Madison, WI (US)

(72) Inventor: Seth K. Williams, Madison, WI (US)

(73) Assignee: Seth K. Williams, Madison, WI (US)

( * ) Notice: Subject to any disclaimer, the term of this patent is extended or adjusted under 35 U.S.C. 154(b) by 0 days.

(21) Appl. No.: 17/408,992

(22) Filed: Aug. 23, 2021

(65) Prior Publication Data

US 2022/0054281 A1 Feb. 24, 2022

Related U.S. Application Data

(60) Provisional application No. 63/069,387, filed on Aug. 24, 2020.

(51) Int. Cl.
*A61F 2/44* (2006.01)
*A61F 2/30* (2006.01)

(52) U.S. Cl.
CPC ............ *A61F 2/4455* (2013.01); *A61F 2/442* (2013.01); *A61F 2002/30331* (2013.01); *A61F 2002/30433* (2013.01)

(58) Field of Classification Search
CPC ...... A61F 2/4455; A61F 2/4611; A61F 2/442; A61F 2002/4435; A61F 2002/30331; A61B 17/7059; A61B 17/80; A61B 17/808
USPC ...................................................... 623/17.16
See application file for complete search history.

(56) References Cited

U.S. PATENT DOCUMENTS

| | | | |
|---|---|---|---|
| 9,474,622 B2 | 10/2016 | McLaughlin et al. | |
| 9,987,145 B2 | 6/2018 | Williams | |
| 10,398,568 B2 | 9/2019 | Williams | |
| 2009/0210062 A1 | 8/2009 | Thalgott et al. | |
| 2010/0168798 A1 | 7/2010 | Clineff et al. | |
| 2011/0251689 A1 | 10/2011 | Seifert et al. | |
| 2011/0301713 A1 | 12/2011 | Theofilos | |
| 2013/0238095 A1 | 9/2013 | Pavento et al. | |
| 2014/0200670 A1* | 7/2014 | Chin ................... | A61B 17/8023 623/17.16 |
| 2014/0228958 A1 | 8/2014 | Niemiec et al. | |
| 2014/0243985 A1 | 8/2014 | Lechmann et al. | |
| 2015/0100126 A1 | 4/2015 | Melkent et al. | |
| 2016/0242925 A1 | 8/2016 | Terrell et al. | |
| 2018/0303629 A1* | 10/2018 | Lauf .................. | A61B 17/8605 |
| 2020/0352739 A1* | 11/2020 | Ouidja ............... | A61B 17/8061 |

* cited by examiner

*Primary Examiner* — Eduardo C Robert
*Assistant Examiner* — Christina Negrellirodriguez
(74) *Attorney, Agent, or Firm* — Bell & Manning, LLC

(57) ABSTRACT

A spine stabilization and fusion system includes a lateral cage having a lateral cage bore hole. The system also includes a lateral cage insertion shaft comprising a leading end, a mid-portion, and a terminal end. A shape of the leading end matches a shape of the lateral cage bore hole such that the leading end mates with the lateral cage bore hole via a friction fit. The system also includes a lateral plate having a lateral plate bore hole and a plurality of holes, where the lateral plate bore hole receives the mid-portion of the lateral cage insertion shaft, and where the plurality of holes receive fasteners to couple the lateral plate to one or more vertebra.

17 Claims, 8 Drawing Sheets

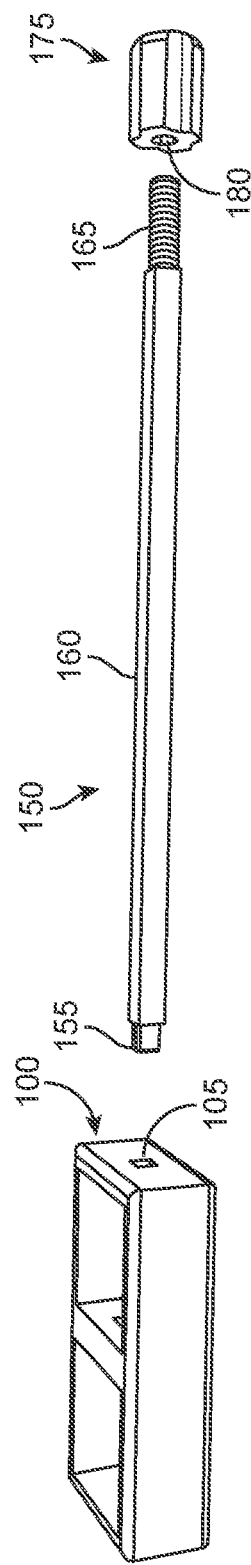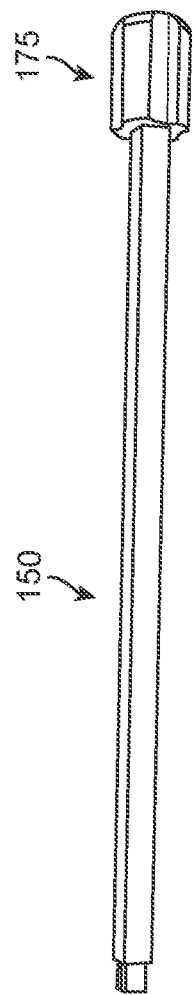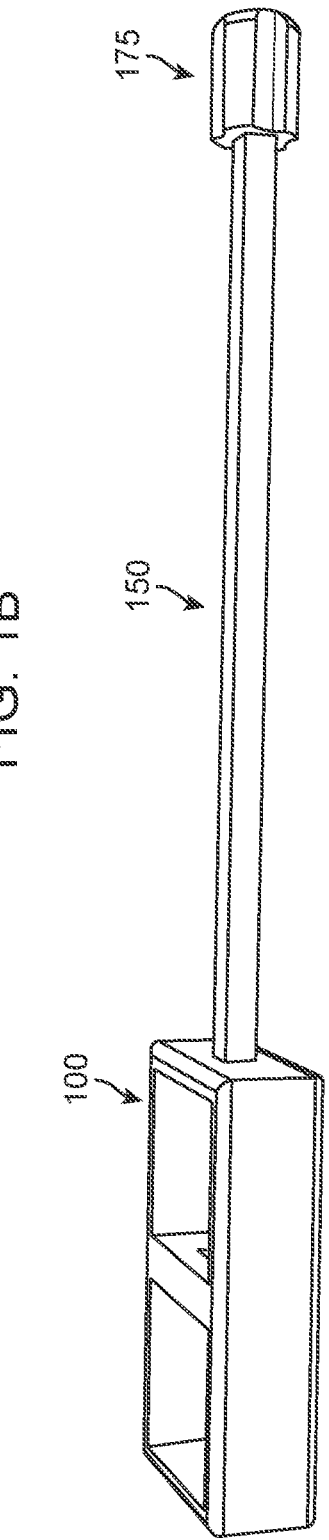
FIG. 1A
FIG. 1B
FIG. 1C

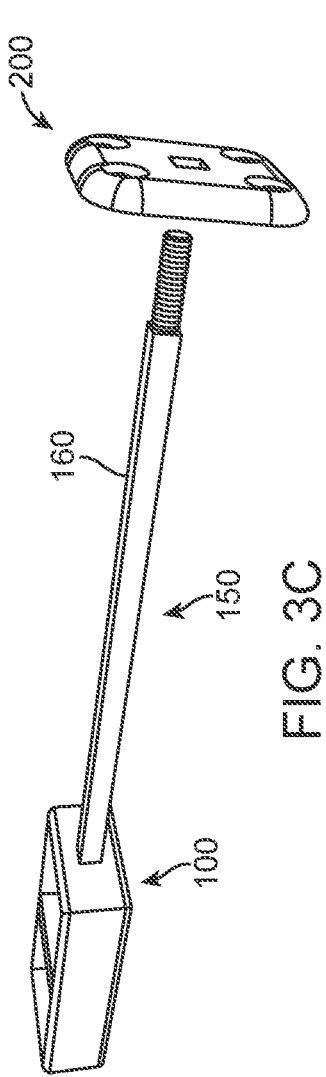
FIG. 3C
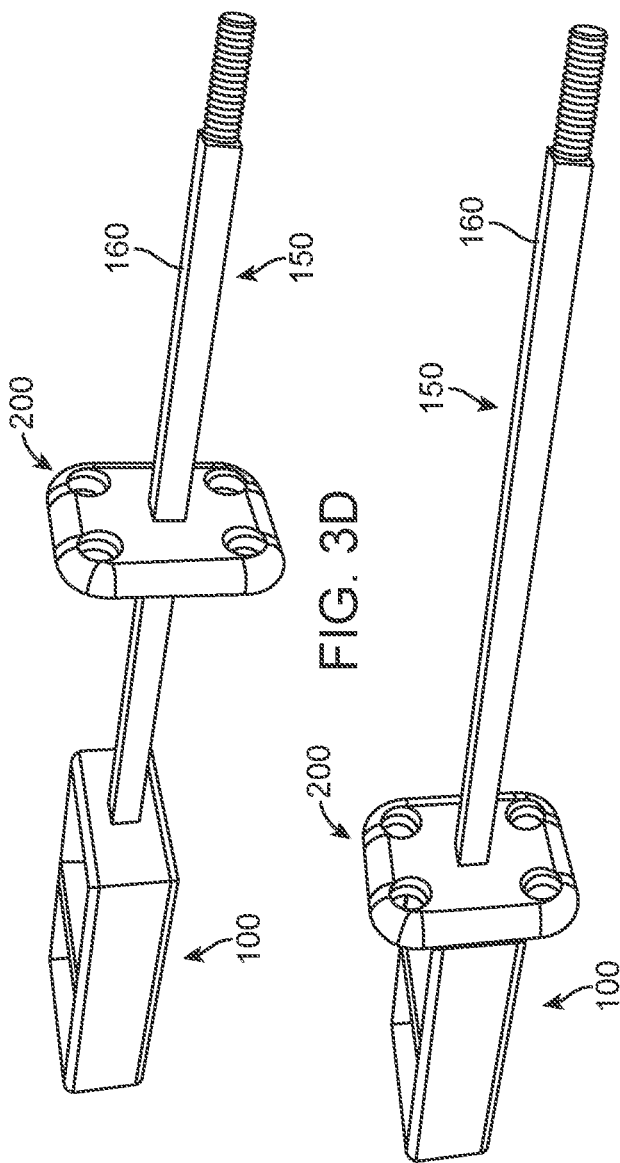
FIG. 3D
FIG. 3E
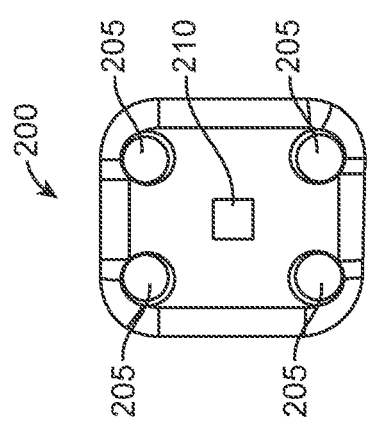
FIG. 3A
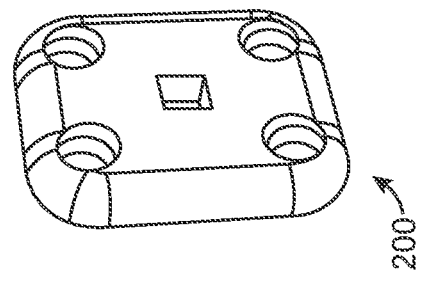
FIG. 3B

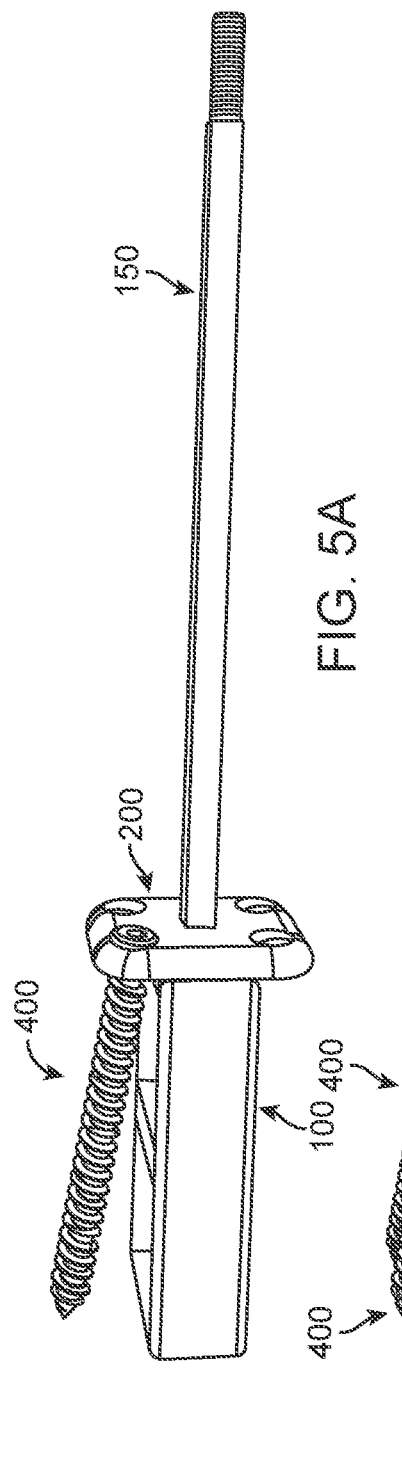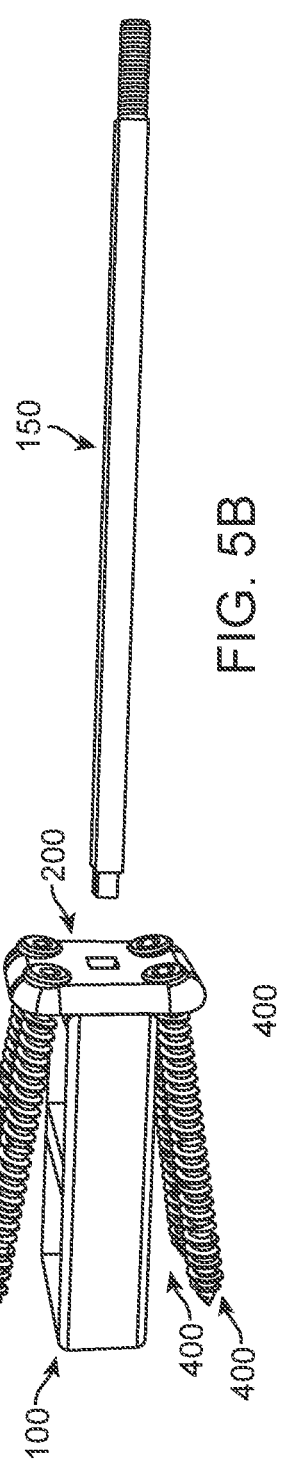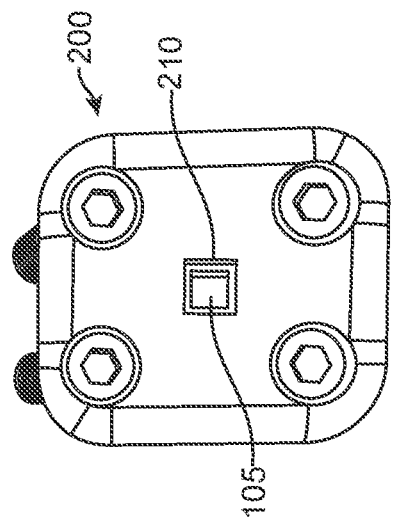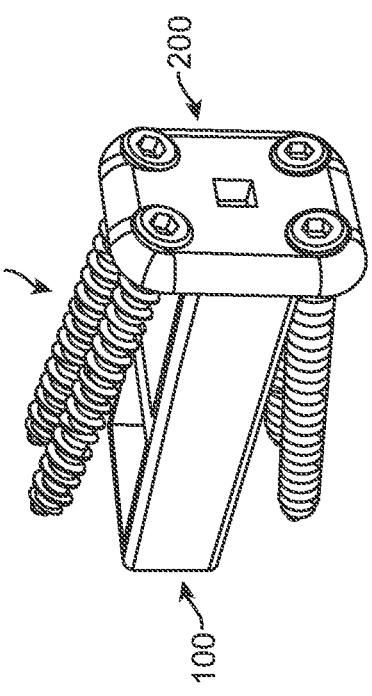
FIG. 5A
FIG. 5B
FIG. 5D
FIG. 5C

US 11,406,511 B2

LATERAL SPINE PLATE WITH LATERAL SPINE CAGE ANCHORING SYSTEM

CROSS-REFERENCE TO RELATED APPLICATION

The present application claims the priority benefit of U.S. Provisional Patent App. No. 63/069,387 filed on Aug. 24, 2020, the entire disclosure of which is incorporated by reference herein.

BACKGROUND

Lumbar spine fusion, or arthrodesis, is a surgical procedure that is performed to fuse two or more vertebrae together. During the procedure, a surgeon places a bone graft or other biological and/or scaffold material that is intended to promote new bone growth between two or more vertebrae. One form of fusion involves removing the majority of the intervertebral disk and replacing the disk with a structural cage that holds bone graft or other material. The spine segments being fused may be stabilized with spinal instrumentation such as a plate and screws. This type of fusion can be performed through a direct lateral or anterolateral retroperitoneal surgical approach. Spinal fusion surgery can be used to relieve nerve generated pain, and to treat ailments such as lumbar degenerative disk disease, spinal stenosis, lumbar spondylolisthesis, and scoliosis.

SUMMARY

An illustrative stabilization and fusion system includes a lateral cage having a lateral cage bore hole. The system also includes a lateral cage insertion shaft comprising a leading end, a mid-portion, and a terminal end. A shape of the leading end matches a shape of the lateral cage bore hole such that the leading end mates with the lateral cage bore hole via a friction fit. The system also includes a lateral plate having a lateral plate bore hole and a plurality of holes, where the lateral plate bore hole receives the mid-portion of the lateral cage insertion shaft, and where the plurality of holes receive fasteners to couple the lateral plate to one or more vertebra.

An illustrative method for performing spine stabilization and fusion includes connecting a lateral cage insertion shaft to a lateral cage. The connecting includes inserting a leading end of the lateral cage insertion shaft into a lateral cage bore hole. The method also includes using the lateral cage insertion shaft to position the lateral cage into a disk space between a lower vertebra and an upper vertebra. The method also includes placing a lateral plate bore hole of a lateral plate over a mid-portion of the lateral cage insertion shaft and sliding the lateral plate along the lateral cage insertion shaft to position the lateral plate adjacent to the lateral cage. The method further includes mounting the lateral plate to the lower vertebra and to the upper vertebra.

Those skilled in the art will appreciate that the summary is illustrative only and is not intended to be in any way limiting. Other aspects, features, and advantages of the devices and/or processes described herein, as defined by the claims, will become apparent in the detailed description set forth herein and taken in conjunction with the accompanying drawings.

BRIEF DESCRIPTION OF THE DRAWINGS

FIG. 1A is an exploded view of a lateral cage, a cage insertion shaft, and an insertion shaft handle in accordance with an illustrative embodiment.

FIG. 1B is a partially exploded view of the lateral cage and the insertion shaft handled mounted to the cage insertion shaft in accordance with an illustrative embodiment.

FIG. 1C is an assembled view of the lateral cage, cage insertion shaft, and insertion shaft handle in accordance with an illustrative embodiment.

FIG. 3A is a plan view of a lateral plate in accordance with an illustrative embodiment.

FIG. 3B is a perspective view of the lateral plate in accordance with an illustrative embodiment.

FIG. 3C depicts the lateral plate in position to be mounted view the cage insertion shaft in accordance with an illustrative embodiment.

FIG. 3D depicts the cage insertion shaft serving as a guide and an anchor for the lateral plate via a bore hole in the lateral plate in accordance with an illustrative embodiment.

FIG. 3E depicts the lateral plate positioned adjacent to the lateral cage via the cage insertion shaft in accordance with an illustrative embodiment.

FIG. 5A depicts a lateral cage and a lateral plate, with a fastener placed through a first hole in the lateral plate to secure the plate to a vertebra in accordance with an illustrative embodiment.

FIG. 5B depicts a cage insertion shaft disengaged from the lateral plate and lateral cage, along with a plurality of fasteners to secure the lateral plate to the vertebra above and below the lateral cage in accordance with an illustrative embodiment.

FIG. 5C is a perspective view of the lateral cage and lateral plate with the cage insertion shaft removed and with a plurality of fasteners securing the plate to the vertebra above and below the lateral cage in accordance with an illustrative embodiment.

FIG. 5D is a front view of the lateral cage and lateral plate with the cage insertion shaft removed and with a plurality of fasteners securing the plate to the vertebra above and below the lateral cage in accordance with an illustrative embodiment.

DETAILED DESCRIPTION

Figure 2A:
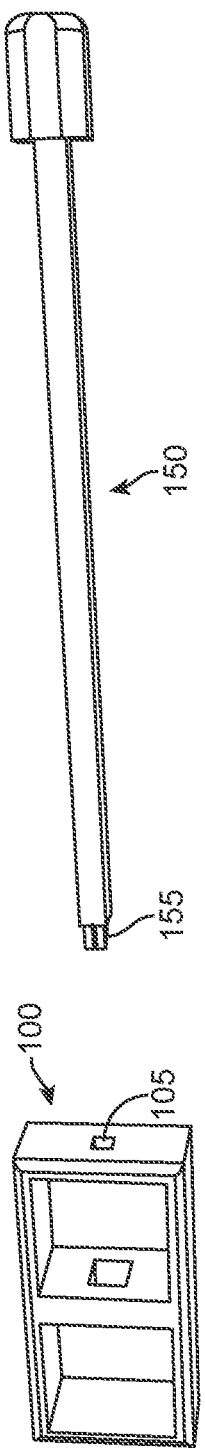
FIG. 2A is a plan perspective view of the lateral cage assembly with the cage insertion shaft detached in accordance with an illustrative embodiment.

The following detailed description is of the best currently contemplated modes of carrying out exemplary embodiments of the subject matter described herein. The description is not to be taken in a limiting sense, but is made merely for the purpose of illustrating the general principles of the described subject matter, since the scope of the subject matter is best defined by the appended claims.

Spinal fusion procedures can be performed via several different approaches, including the lateral retroperitoneal approach or anterolateral retroperitoneal approach. Regardless of the approach used, traditional interbody spinal fusion procedures involve removal and replacement of an intervertebral disk with a cage that is used to provide structural support to the patient in place of the removed disk. The cage usually holds bone graft or other material that promotes a bony fusion, and typically fills some or all of the space that was previously occupied by the removed disk. The cage may be held in place and stabilized by a plate that is mounted outside of the disk space in a vertical position that is substantially perpendicular to both the disk space and the cage. The plate is secured by screws or fasteners bored into the lateral sides of vertebral bodies above and below the disk space.

Such spinal fusion techniques are prone to problems with lateral plate rotation and/or migration in a cephalad/caudal and/or anterior posterior direction during plate placement because there is not a reliable method to provisionally hold the plate in place during fastener placement through the plate into bone. Provisional fasteners placed into bone are often not strong enough to reliably secure the plate during drilling or awling the fastener pathway, and then placing the fastener. One method to counter this plate movement during fastener placement is to secure the plate to the cage, but if this is a permanent connection between the lateral cage and the lateral plate, then the lateral cage and lateral plate function as a single implant and the biomechanical forces from human activity are theoretically distributed throughout the conjoined cage and plate, and this may be undesirable for some patients and situations. An alternative is to temporarily and reversibly secure the plate to the cage and insert the two implants as a unit, then place the fasteners, followed by decoupling the cage and plate. However, in order to do this, the surgeon must anticipate the need for a lateral plate and must plan for the size of the plate prior to implanting the cage, which may pose problems if the surgeon decides to place the plate only after the cage is inserted, or if a plate of incorrect size is chosen. In view of these problems, the inventor has designed a new system that utilizes a lateral cage in conjunction with a lateral plate that is guided into place by a shaft that is used to insert the cage, or by a shaft that is temporarily secured to the cage after cage insertion. The shaft guides the plate into position, and due to the geometry of the shaft and reciprocal geometry of the shaft bore in the plate, the plate is anchored in position so there is no plate movement during drilling or awling. Additionally, when the shaft is removed, the plate is automatically decoupled from the cage to allow for separate biomechanical forces on the cages and plate or plates during patient activity.

Broadly, the embodiments described herein provide a spinal fusion lateral plate that may temporarily anchor to a lateral cage via a shaft, which prevents cage rotation and/or migration during establishment of the fastener pathways with a drill or awl and fastener placement. The spinal plate described herein solves the problem of plate migration and/or rotation during the process of fastener placement because the lateral plate is at least temporarily anchored to the lateral cage during the fastener placement process.

FIG. 1A depicts a lateral or side view of a lateral cage 100, in accordance with an illustrative embodiment. A lateral cage bore hole 105 is configured to receive a leading end 155 of a cage insertion shaft 150, in accordance with an illustrative embodiment. The mid-portion of cage insertion shaft 150 may be of variable geometry, here depicted as square 160. In alternative embodiments, a different cross-sectional geometry of the mid-portion of the cage insertion shaft 150 may be used, such as circular, rectangular, ovular, triangular, etc. A terminal end or section of cage insertion shaft 150 is depicted in FIG. 1 as a male threaded portion 165, is configured to receive an insertion handle 175, via a female threaded portion 180 of the insertion handle 175. As shown, the leading end 155 of the cage insertion shaft 150 has a smaller circumference than the mid-portion of the shaft. As such, the mid-portion acts as a stop to control the distance which the cage insertion shaft 150 can be inserted into the lateral cage 100. The leading end 155 is square to prevent rotation once inserted into the lateral cage 100. Alternatively, different shapes may be used for the leading end 155 such as triangular, rectangular, star-shaped, ovular, etc.

FIG. 1B depicts a lateral or side view of a lateral cage 100, in accordance with an illustrative embodiment. Insertion handle 175 has been attached to insertion shaft 150. As discussed herein, the insertion handle 175 is removable to enable a lateral plate to slide down a length of the cage insertion shaft 150 for mounting of the lateral plate. FIG. 1C depicts a lateral or side view of the lateral cage 100, in accordance with an illustrative embodiment. Insertion handle 175 is attached to insertion shaft 150, and shaft 150 is attached to the lateral cage 100 via an interference fit. In alternative embodiments, the cage insertion shaft 150 can be attached to the lateral cage 100 via threads, tines, or other alternative mechanisms of attachment.

Figure 2B:
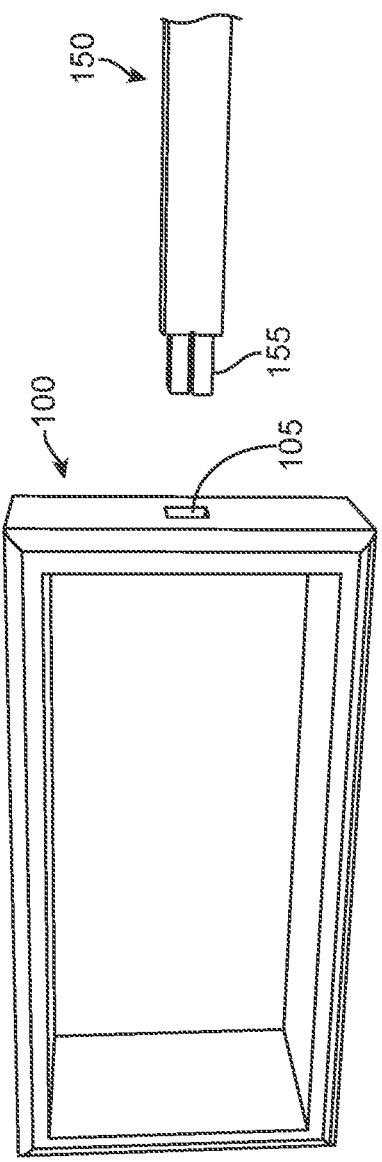
FIG. 2B is a close-up view of the interface between the lateral cage and the cage insertion shaft in accordance with an illustrative embodiment.
Figure 2C:
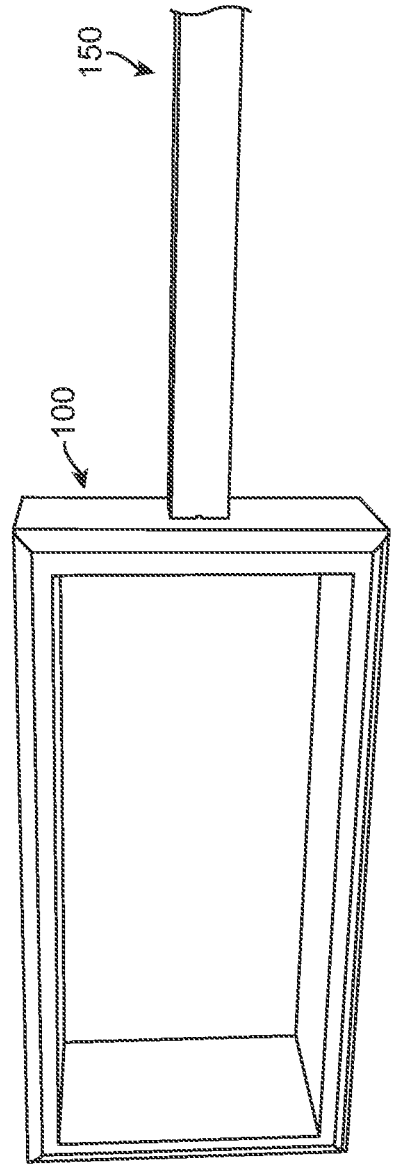
FIG. 2C depict is a close-up view of the cage insertion shaft mounted to the lateral cage in accordance with an illustrative embodiment.

FIG. 2A is a top or superior view of lateral cage 100 with bore hole 105, and insertion shaft 150 with leading end 155 that serves as a mechanism of attachment to bore hole 105, in accordance with an illustrative embodiment. FIG. 2B depicts a close-up view of lateral cage 100 with bore hole 105, and insertion shaft 150 with leading end 155 that serves as a mechanism of attachment to bore hole 105, in accordance with an illustrative embodiment. FIG. 2C is a top or superior view of lateral cage, with insertion shaft 150 attached to cage 100 via bore hole 105 (from FIG. 2B) receiving leading portion of insertion handle 155 (from FIG. 2B), in accordance with an illustrative embodiment. As shown, the shape of the bore hole 105 (i.e., square in this embodiment) matches the shape of the leading end 155 of the cage insertion shaft 150. In alternative embodiments, different shapes may be used for the bore hole 105 and the leading end 155.

FIG. 3A is a first view of a lateral plate 200 in accordance with an illustrative embodiment. FIG. 3B is a second view of the lateral plate 200 in accordance with an illustrative embodiment. FIG. 3C depicts the cage insertion shaft mounted to the lateral cage with the lateral plate positioned to be mounted onto the cage insertion shaft in accordance with an illustrative embodiment. FIG. 3D depicts the lateral plate mounted on the cage insertion shaft in accordance with an illustrative embodiment. FIG. 3E depicts the lateral plate mounted on the cage insertion shaft and positioned adjacent to the lateral cage in accordance with an illustrative embodiment.

Still reference to FIG. 3, holes 205 accommodate screws or fasteners that pass through the lateral plate 200 to secure it to bone. Although four holes are depicted, in alternative embodiments, a lateral plate may include additional or fewer holes to accommodate screws or fasteners. Bore hole 210 in lateral plate 200 accommodates the cage insertion shaft 150 (from FIG. 3C) to guide the lateral plate 200 into position, adjacent to the lateral cage 100 (from FIG. 3E). Due to the matching geometry of the mid-portion of the cage insertion shaft 150 with bore hole 210, lateral plate 200 is held in a fixed position, preventing rotation of lateral plate 200 with respect to lateral cage 100 during the process of securing lateral plate 200 to vertebral bodies. In addition to preventing rotation of plate 200 with respect to the lateral cage 100, the cage insertion shaft 150, by virtue of its engagement with plate bore hole 210 but irrespective of geometry, prevents cephalad/caudal and/or anterior/posterior movement of lateral plate 200 with respect to lateral cage 100 during the fastener pathway and fastener insertion process. The cage insertion shaft 150 thus temporarily secures the lateral plate 200 to the lateral cage 100 such that the lateral plate 200 can be mounted in a desired position relative to the lateral cage 100.

Figure 4A:
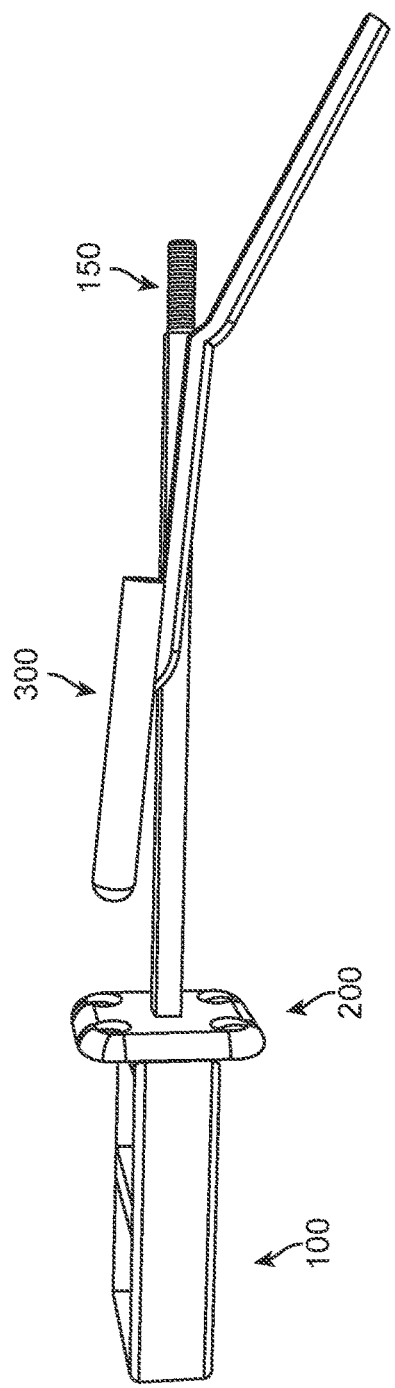
FIG. 4A depicts a drill/awl guide for use with the lateral cage assembly in accordance with an illustrative embodiment.

FIG. 4A depicts a lateral plate 200 that has been guided into position adjacent to lateral cage 100 via cage insertion handle 150, in accordance with an illustrative embodiment. A drill or awl guide 300 is positioned to guide a drill or awl in establishing fastener trajectory. In an alternative embodiment, the holes in the lateral plate 200 can be positioned at angles to help control the fastener trajectory such that the fasteners are not parallel to the lateral cage 100. For example, holes in the lateral plate positioned above the lateral cage may be angled upward and outward (or inward) in an effort to ensure that the fasteners enter the vertebra above the lateral cage at a desired angle. Similarly, the holes in the lateral plate positioned below the lateral cage may be angled downward and outward (or inward) in an effort to ensure that the fasteners enter the vertebra below the lateral cage at a desired angle. In such an implementation, the drill/awl guide 300 can be used to help ensure that the fasteners maintain the angled orientation associated with each of the holes in the lateral plate.

Figure 4B:
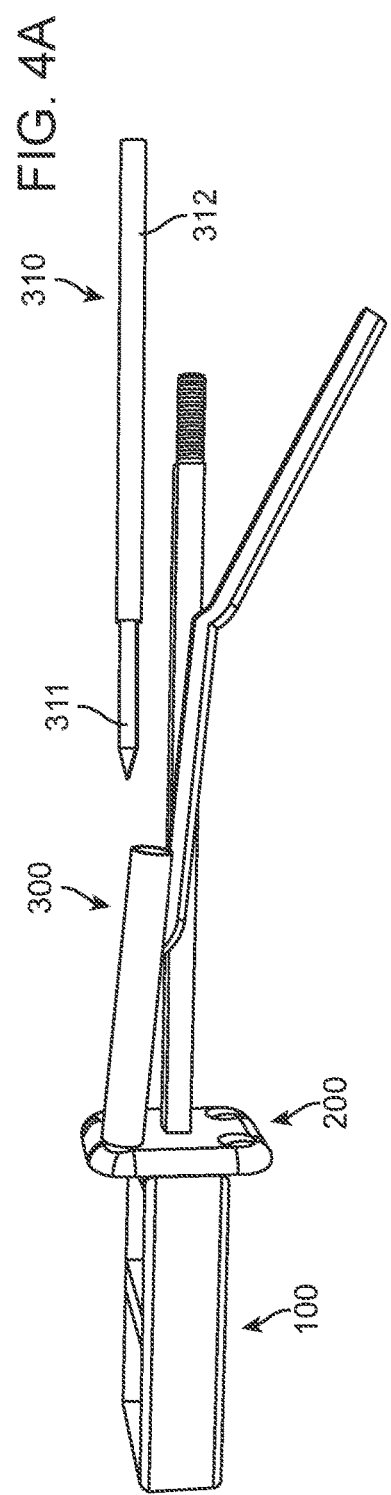
FIG. 4B depicts the drill/awl guide positioned over a lateral plate with an awl positioned for insertion in accordance with an illustrative embodiment.

FIG. 4B depicts lateral plate 200 that has been guided into position adjacent to lateral cage 100 via insertion handle 150, in accordance with an illustrative embodiment. Drill or awl guide 300 is now positioned in a fastener bore in plate 200, to guide a drill or awl in establishing fastener trajectory into a vertebra. Drill or awl 310 is depicted, with drill or awl shaft 312 and leading end 311. An end of the drill or awl guide 300 can mate with the fastener hole via a friction fit.

Figure 4C:
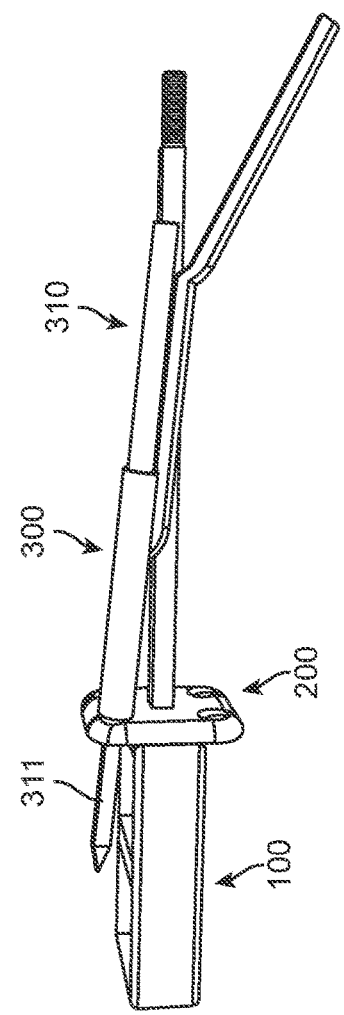
FIG. 4C depicts the awl positioned within the drill/awl guide in accordance with an illustrative embodiment.

FIG. 4C depicts lateral plate 200 that has been guided into position adjacent to lateral cage 100 via insertion handle 150, in accordance with an illustrative embodiment. Drill or awl guide 300 is now positioned in a fastener bore in plate 200, to guide a drill or awl in establishing fastener trajectory into a vertebra. Drill or awl 310 is depicted, with drill or awl leading end 311 shown as fully inserted through the plate 200, which would be into vertebral bone. As shown, the drill/awl guide 300 includes a receptacle shaped to receive a drill bit or awl. Also, the drill/awl guide 300 includes an offset alignment bar mounted to an external surface of the receptacle and running parallel to the receptacle to help guide the drill bit or awl into the receptacle, and an angled handle that extends out from the offset alignment bar.

In one embodiment, the offset alignment bar of the guide 300 can include an opening therethrough that is sized and shaped to be received by the mid-portion of the insertion handle 150, similar to how the lateral plate is received by the mid-portion of the insertion handle 150. In such an embodiment, the mid-portion of the insertion handle 150 acts to hold the guide 300 in place over the holes of the lateral plate at a desired angle during a drilling or awling process. To drill each subsequent hole, the guide 300 can be removed from the mid-portion of the insertion handle, rotated 90 degrees, and reinserted onto the insertion handle such the receptacle which receives the drill bit or awl is aligned with another hole in the lateral plate. Alternatively, instead of removing the guide 300 and rotating it 90 degrees to access subsequent holes, the receptacle of the guide can be mounted such that the receptacle is able to rotate 360 degrees about offset alignment bar. In such an implementation, the user can rotate the receptacle to a desired orientation (i.e., relative to a hole) and lock the receptacle at the desired orientation for the drilling or awling process. In addition to rotating, the receptacle can also be mounted such that it pivots relative to the offset alignment bar for angle adjustment.

FIG. 5A depicts lateral plate 200 that has been guided into position adjacent to lateral cage 100 via insertion handle 150, in accordance with an illustrative embodiment. Screw or fastener 400 has been placed into the screw or fastener pathway in the vertebra above/cephalad to lateral cage 100. As discussed above, the screw or fastener pathway can be established by drill or awl 310 (from FIG. 4C). As shown, the handle has been removed from the cage insertion shaft 150 to accommodate the lateral plate 200.

FIG. 5B depicts lateral plate 200 that has been guided into position adjacent to lateral cage 100 via insertion handle 150, in accordance with an illustrative embodiment. Multiple screws or fasteners 400 have now been placed through bore holes 205 (from FIG. 3A) in plate 200 into the screw or fastener pathways in the vertebra above/cephalad and below/caudal to lateral cage 100. The screw or fastener pathways can be established by the drill or awl 310 (from FIG. 4C). Insertion shaft 150 has now been removed from its connection to lateral plate 200 and lateral cage 100, thus decoupling lateral cage 200 from lateral cage 100.

FIG. 5C depicts lateral plate 200 that is in a position adjacent to lateral cage 100, in accordance with an illustrative embodiment. Multiple screws or fasteners 400 have been placed through bore holes 205 (from FIG. 3A) in plate 200 into the screw or fastener pathways in the vertebra above/cephalad and below/caudal to lateral cage 100. Insertion shaft 150 has been removed from its connection to lateral plate 200 and lateral cage 100, thus decoupling lateral cage 200 from lateral cage 100.

FIG. 5D shows a lateral view of plate 200, with plate bore hole 210 visible, and lateral cage bore hole 105 visible, demonstrating that in this embodiment, lateral plate 200 is not physically attached to lateral cage 100 (not shown, as lateral cage 100 is hidden from view in this depiction). As shown, the lateral cage bore hole 105 aligns with the plate bore hole 210. As such, in an alternative embodiment, a locking fastener can be positioned through the lateral plate bore hole 210 and the lateral cage bore hole 105 to couple the two components to one another. In one implementation, the locking fastener can have a first portion sized to fit within and frictionally mate with the bore hole in the lateral cage, and a second portion sized to fit within and frictionally mate with the bore hole in the lateral plate.

Figure 6B:
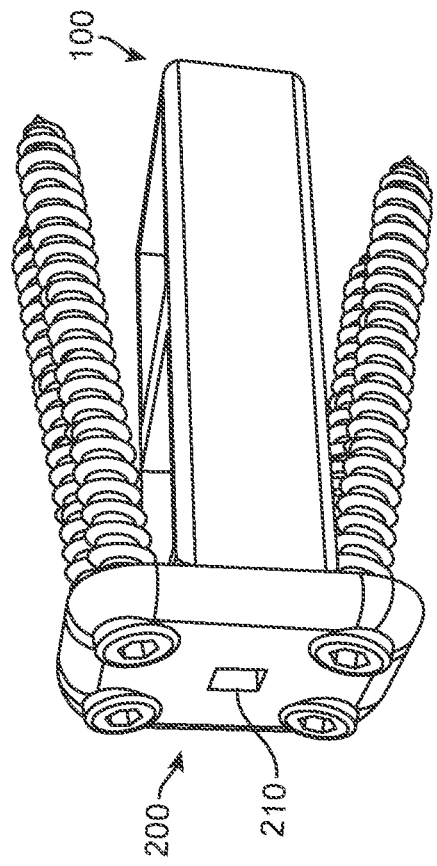
FIG. 6B depicts the connector in position to be used to establish a permanent connection between the lateral plate and the lateral cage, in accordance with an illustrative embodiment.
Figure 6C:
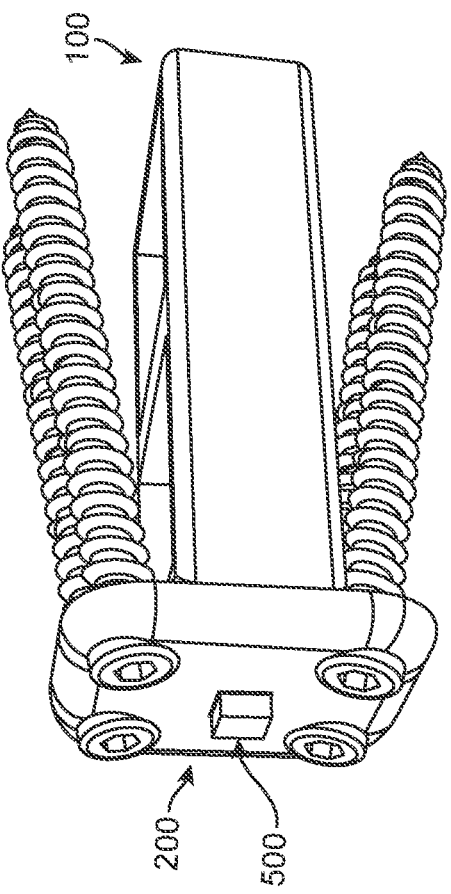
FIG. 6C depicts the connector inserted into the lateral plate and the lateral cage in accordance with an illustrative embodiment.
Figure 6A:
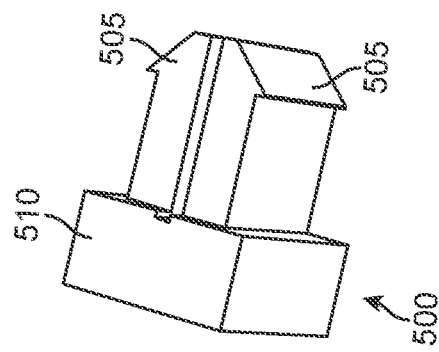
FIG. 6A depicts a connector 500 that may be used to establish a permanent connection between a lateral plate 200 (from FIG. 6B) and lateral cage 100 (from FIG. 6B), in accordance with an illustrative embodiment.

FIG. 6A depicts a connector 500 that may be used to establish a permanent connection between a lateral plate 200 (from FIG. 6B) and lateral cage 100 (from FIG. 6B), in accordance with an illustrative embodiment. Connector 500 is optionally used at the discretion of the surgeon. In this embodiment, an inner portion of the connector 500 includes extensions 505 that insert into and through lateral plate bore hole 210, and into lateral cage bore hole 105 such that the inner portion of the connector 500 is secured within the lateral cage bore hole 105. Specifically, each of the extensions 505 includes an angled end, a portion of which extends outward past the main body of the extension 505 to create a flange on each extension. Additionally, there is a gap between the extensions 505 that allows the extensions 505 to flex toward one another as the connector 500 is inserted through the lateral cage bore hole 105. Upon insertion of the extensions 505 of the connector 500 into the lateral cage bore hole, the flanges on the angled ends of each extension 505 contact an inner surface of the lateral cage bore hole 105, and the gap between extensions 505 allows the extensions to flex toward one another such that the extensions (and flanges formed on the angled ends thereof) can pass through the lateral cage bore hole. Once the flanges of the extensions pass through the lateral cage bore hole, the gap allows the extensions 505 to expand outward and return to their original orientation. As a result, the flanges on the angled ends of the extensions 505 rest upon an inner surface of the front plate of the lateral cage, thereby securing the connector 500 to the lateral cage.

An outer portion 510 of the connector 500 is integrally connected to the inner portion, and in one embodiment the outer portion 510 is sized larger than the lateral plate bore hole such that the outer portion helps secure the lateral plate to the lateral cage. Thus, when fully inserted, the connector 500 engages a lateral plate and lateral cage in a manner that permanently couples them. FIG. 6B depicts the connector 500 in position to be used to establish a permanent connection between the lateral plate 200 and the lateral cage 100, in accordance with an illustrative embodiment. FIG. 6C depicts the connector 500 inserted into the lateral plate 200 and the lateral cage 100 in accordance with an illustrative embodiment.

Figure 7B:
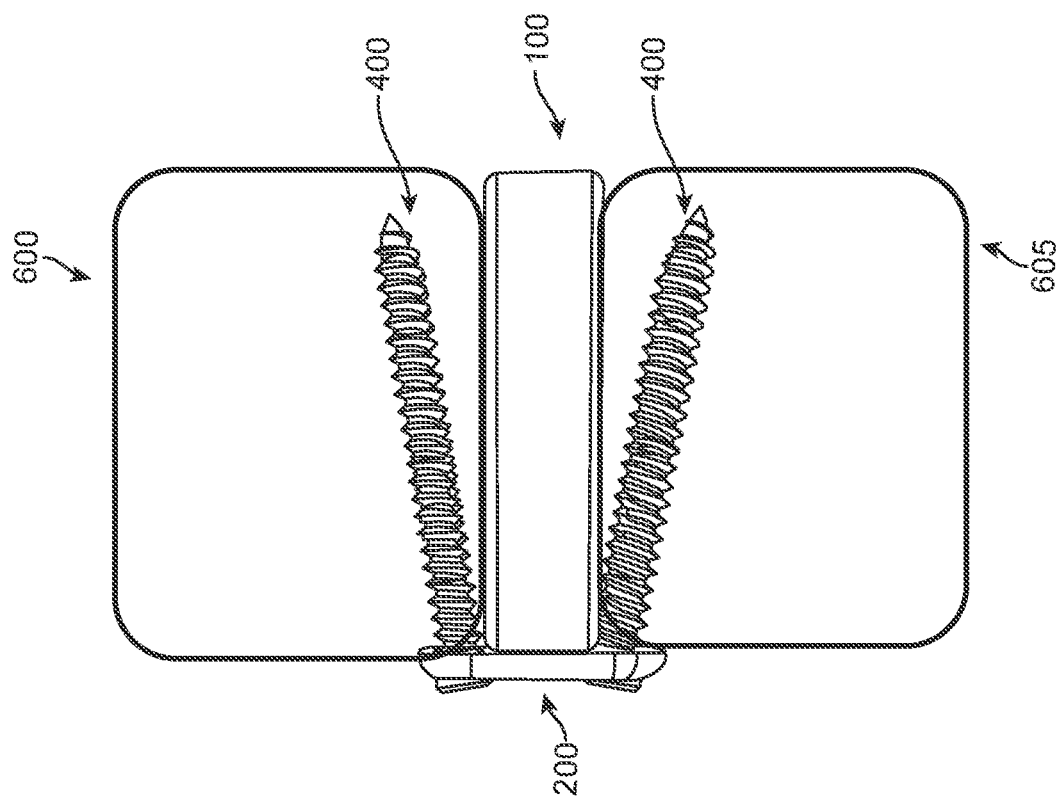
FIG. 7B depicts a lateral plate, a lateral cage, and screws, in a final construct once surgery has been completed, in accordance with illustrative embodiments.
Figure 7A:
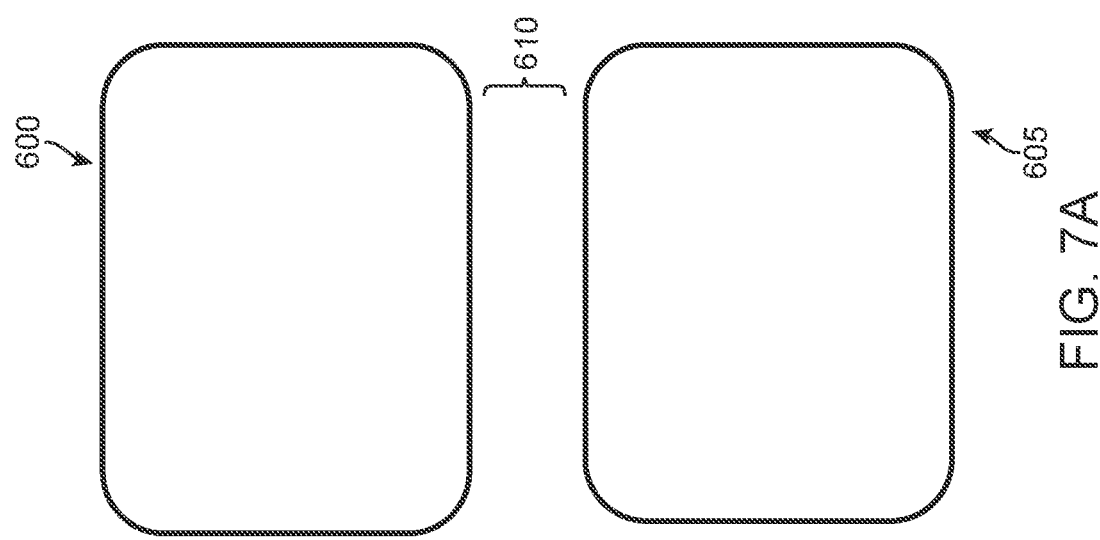
FIG. 7A depicts a cephalad vertebral body, a caudal vertebral body, and a disk space to be fused in accordance with an illustrative embodiment.

FIG. 7A depicts a cephalad vertebral body 600, a caudal vertebral body 605, and a disk space to be fused 610 in accordance with an illustrative embodiment. FIG. 7B depicts a lateral plate 200, a lateral cage 100, and screws 400, in a final construct once surgery has been completed, in accordance with illustrative embodiments. Lateral cage 100 is located within disk space 610 (from FIG. 7A), lateral plate 200 sits adjacent to vertebral bodies 600 and 605, and screws or fasteners 400 have been inserted into a cephalad vertebral body 600 and a caudal vertebral body 605.

In an illustrative embodiment, to utilize the described system, the lateral cage is inserted into a space adjacent to an upper vertebra and a lower vertebra. The lateral cage can be inserted using the cage insertion shaft. Specifically, the handle can be mounted onto the cage insertion shaft and a leading end of cage insertion shaft can mate with the bore hole in the lateral cage. The user can then manipulate the lateral cage into any desired position between the vertebra. The user can then remove the handle from the cage insertion shaft, and a lateral plate can be slid down the insertion shaft via a bore hole in the lateral plate that mates with a mid-portion of the shaft to prevent rotation of the lateral plate. Once the lateral plate is slid onto the mid-portion of the shaft, the handle can be reattached to the shaft such that the shaft is easier to hold and manipulate. The plate is then positioned adjacent to the upper and lower vertebra and a drill/awl guide is used to control a trajectory at which holes are made in the upper/lower vertebra using a drill or awl. Fasteners are placed through holes in the lateral plate and into the holes made in the vertebra at the desired trajectories. The shaft can then be removed from both the lateral cage bore hole and the lateral plate bore hole to decouple the lateral plate from the lateral cage.

Figure 8:
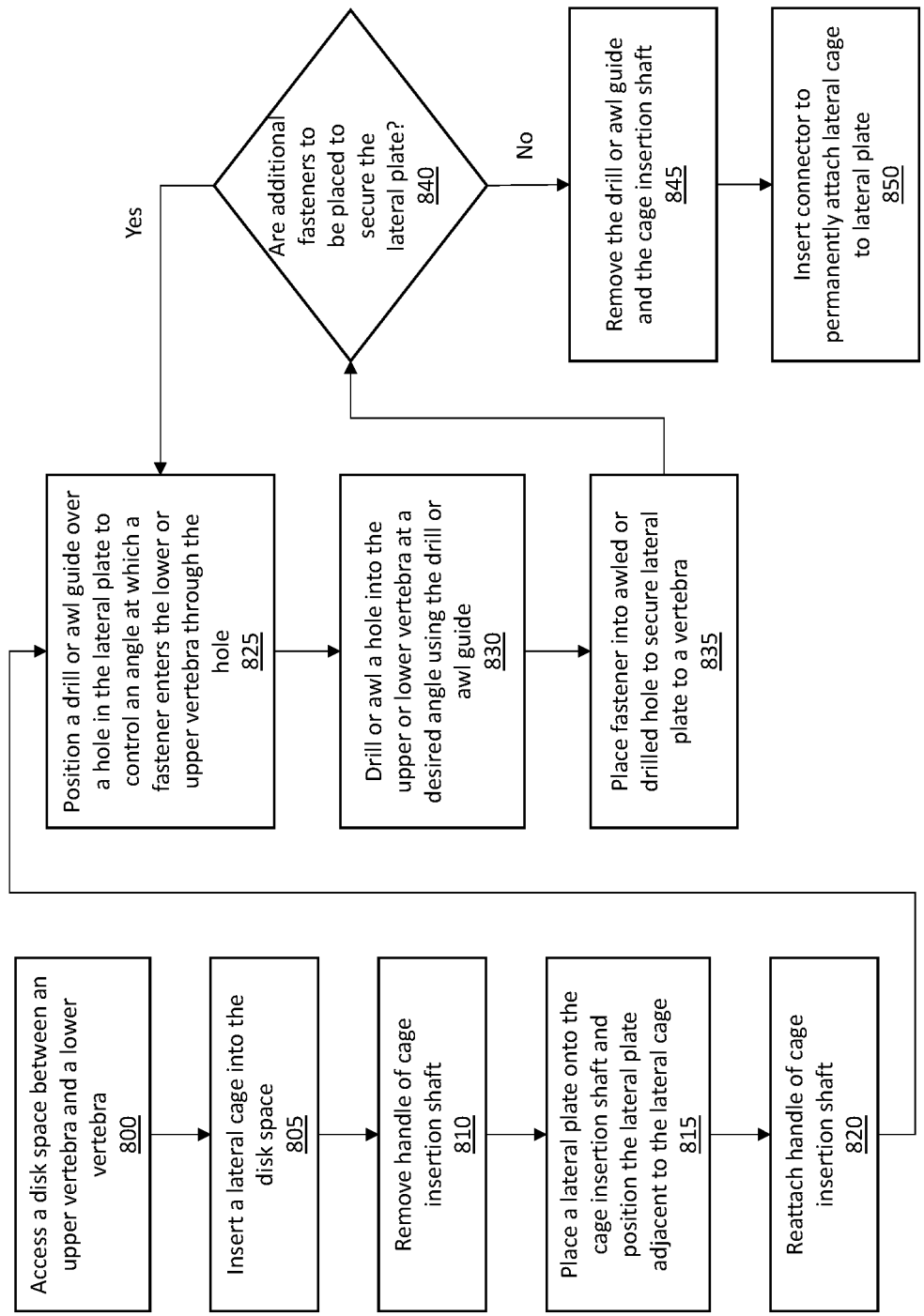
FIG. 8 is a flow diagram depicting operations performed to insert and anchor a lateral cage in accordance with an illustrative embodiment.

FIG. 8 is a flow diagram depicting operations performed to insert and anchor a lateral cage in accordance with an illustrative embodiment. In alternative embodiments, fewer, additional, and/or different operation may be performed. Also, the use of a flow diagram is not meant to be limiting with respect to the order of operations performed. In an operation 800, a disk space between an upper vertebra and a lower vertebra is accessed. Accessing the disk space can include making one or more incisions, and removing an existing vertebra that is to be replaced by a lateral cage. The disk space can be accessed using any techniques known in the art.

In an operation 805, a lateral cage is inserted into the disk space. In some embodiments, a cage insertion shaft may be used to assist with the insertion. For example, a leading end of the cage insertion shaft can mate with a bore hole in the lateral cage such that the cage insertion shaft is (removably) connected to the lateral cage. The user can then manipulate the lateral cage into any desired position between the upper and lower vertebra. Alternatively, any other insertion/placement techniques known in the art may be used. Regardless of how the lateral cage is inserted, the cage insertion shaft can be connected to the lateral during or subsequent to the operation 805. In an operation 810, a handle of the cage insertion shaft is removed, mounted to the lateral cage. In an illustrative embodiment, the handle of the cage insertion shaft can be unthreaded from an end of the shaft.

In an operation 815, a lateral plate is positioned on the cage insertion shaft and is positioned adjacent to the lateral cage. Specifically, a bore hole on the lateral plate receives a mid-portion of the cage insertion shaft. In an illustrative embodiment, an interior of the bore hole on the lateral plate and a cross section of the mid-portion of the cage insertion shaft have matching non-circular geometries such that the bore hole and the shaft mate with one another. The matching non-circular geometries prevent rotation of the lateral plate relative to the cage insertion shaft and the lateral cage. In an operation 820, the handle of the cage insertion shaft is reattached to allow the shaft to be more easily held and manipulated. In an alternative embodiment, operation 820 may not be performed.

In an operation 825, a drill or awl guide is positioned over a hole in the lateral plate to control an angle at which a fastener enters the lower or upper vertebra through the hole. In an operation 830, a hole is awled or drilled into the lower or upper vertebra using the awl or drill guide. In an operation 835, a fastener is placed into the awled or drilled hole to secure the lateral plate to a vertebra. In an operation 840, a determination is made regarding whether additional fasteners are to be placed to secure the lateral plate to the vertebrae. If another fastener is to be inserted, the operations 825-835 are repeated. If another fastener is not to be inserted, the drill or awl guide and the cage insertion shaft are removed in an operation 845. In an operation 850, a connector is inserted to permanently attach the lateral cage to the lateral plate. In an alternative embodiment in which the lateral plate is to remain detached from the lateral cage, the operation 850 is not performed.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents

What is claimed is:

1. A spine stabilization and fusion system comprising:
    a lateral cage having a lateral cage bore hole;
    a lateral cage insertion shaft comprising a leading end, a mid-portion, and a terminal end, wherein a shape of the leading end matches a shape of the lateral cage bore hole such that the leading end mates with the lateral cage bore hole via a friction fit;
    a lateral plate having a lateral plate bore hole and a plurality of holes, wherein the lateral plate bore hole receives the mid-portion of the lateral cage insertion shaft, and wherein the plurality of holes receive fasteners to couple the lateral plate to one or more vertebra;
    a guide to control an angle of insertion of the fasteners, wherein the guide includes a receptacle that mates with a hole of the plurality of holes and that is sized to receive a drill bit or an awl; and
    an offset alignment bar mounted to an external surface of the receptacle of the guide, wherein the offset alignment bar includes an opening therethrough that is sized and shaped to be received by the mid-portion of the lateral cage insertion shaft.

2. The spine stabilization and fusion system of claim 1, wherein the terminal end of the lateral cage insertion shaft is configured to receive a removable handle to allow the lateral plate to mount to the mid-portion of the lateral cage insertion shaft.

3. The spine stabilization and fusion system of claim 2, wherein the terminal end of the lateral cage insertion shaft comprises a male threaded end configured to receive a threaded portion of the removable handle.

4. The spine stabilization and fusion system of claim 1, wherein the mid-portion of the lateral cage insertion shaft has a larger circumference than the leading end of the lateral cage insertion shaft.

5. The spine stabilization and fusion system of claim 1, wherein the shape of the leading end and the shape of the lateral cage bore hole are non-circular to provide the friction fit.

6. The spine stabilization and fusion system of claim 1, further comprising a connector configured to secure the lateral plate to the lateral cage.

7. The spine stabilization and fusion system of claim 6, wherein the connector includes an inner portion that mates with the lateral cage bore hole and an outer portion that mates with the lateral plate bore hole.

8. The spine stabilization and fusion system of claim 7, wherein the inner portion includes extensions that are separated by a gap.

9. The spine stabilization and fusion system of claim 8, wherein each of the extensions has an angled end.

10. The spine stabilization and fusion system of claim 9, wherein the angled end includes a flange that extends out from a main body of the extension.

11. The spine stabilization and fusion system of claim 10, wherein the flange is configured to rest upon an inner surface of a front plate of the lateral cage.

12. The spine stabilization and fusion system of claim 10, wherein the gap allows the extensions to flex toward one another as the extensions pass through the lateral cage bore hole.

13. The spine stabilization and fusion system of claim 1, wherein the offset alignment bar is mounted such that the offset alignment bar runs parallel to the receptacle to help guide the drill bit or the awl into the receptacle.

14. A method for performing spine stabilization and fusion, the method comprising:
    connecting a lateral cage insertion shaft to a lateral cage, wherein the connecting includes inserting a leading end of the lateral cage insertion shaft into a lateral cage bore hole;
    using the lateral cage insertion shaft to position the lateral cage into a disk space between a lower vertebra and an upper vertebra;
    placing a lateral plate bore hole of a lateral plate over a mid-portion of the lateral cage insertion shaft and sliding the lateral plate along the lateral cage insertion shaft to position the lateral plate adjacent to the lateral cage;
    positioning a guide to control an angle of insertion of a fastener into a hole of the lateral plate, wherein the guide includes a receptacle that mates with the hole and that is sized to receive a drill bit or an awl, wherein the guide includes an offset alignment bar mounted to an external surface of the receptacle, and wherein positioning the guide includes mounting the offset alignment bar on the mid-portion of the lateral cage insertion shaft; and
    mounting the lateral plate to one of the lower vertebra and the upper vertebra with the fastener.

15. The method of claim 14, further comprising removing a handle of the lateral cage insertion shaft such that the lateral plate bore hole of the lateral plate can be positioned over the mid-portion of the lateral cage insertion shaft.

16. The method of claim 14, further comprising placing a connector through the lateral cage bore hole and the lateral plate bore hole to secure the lateral cage to the lateral plate.

17. The method of claim 14, wherein a cross-section of the mid-portion of the lateral cage insertion shaft and an interior of the lateral plate bore hole have a matching non-circular shape such that placing the lateral plate bore hole of the lateral plate over the mid-portion of the lateral cage insertion shaft prevents rotation of the lateral plate relative to the mid-portion of the lateral cage insertion shaft.

* * * * *